United States Patent [19]

Blake

[11] Patent Number: 4,737,148

[45] Date of Patent: Apr. 12, 1988

[54] FILTERED T COUPLING

[75] Inventor: Larry W. Blake, Irvine, Calif.

[73] Assignee: Allergan Surgical, Irvine, Calif.

[21] Appl. No.: 863,117

[22] Filed: May 14, 1986

[51] Int. Cl.$^4$ ................................................ A61M 1/00
[52] U.S. Cl. ................................. 604/126; 604/119;
604/902; 137/526
[58] Field of Search .............. 604/126, 129, 119, 283,
604/284, 902; 55/478, 480; 137/526

[56] References Cited

U.S. PATENT DOCUMENTS

| | | | |
|---|---|---|---|
| 3,598,124 | 8/1971 | Andersen | 604/129 |
| 3,811,467 | 5/1974 | Jones | 137/526 |
| 3,830,241 | 8/1974 | Dye et al. | 137/526 |
| 3,834,124 | 9/1974 | Ichikawa | 604/126 |
| 3,967,605 | 7/1976 | Dolfi, Sr. | 137/526 |
| 4,391,599 | 7/1983 | Jenkins | 604/126 |
| 4,418,944 | 12/1983 | Haines et al. | 604/119 |
| 4,508,533 | 4/1985 | Abramson | 604/126 |
| 4,534,542 | 8/1985 | Russo | 604/119 |
| 4,560,144 | 12/1985 | Williams et al. | 604/119 |

FOREIGN PATENT DOCUMENTS 1399435  9/1975  United Kingdom .............. 604/129

OTHER PUBLICATIONS

"Coopervision 8000" and "Cavitron Kelman Model 6500" drawings.

United Sonics Extra Plus (designated "United Sonics") drawing.

Primary Examiner—C. Fred Rosenbaum
Assistant Examiner—Gene B. Kartchner
Attorney, Agent, or Firm—Knobbe, Martens, Olson & Bear

[57] ABSTRACT

A fluid T-coupling comprising a through fluid flow path, and an intersecting vent path, wherein the vent path is integrally molded within the filtered bayonet connector to be used with an aspirator to control the level of vacuum communicated to an irrigation/aspiration handpiece during eye surgery.

13 Claims, 2 Drawing Sheets

FILTERED T COUPLING

BACKGROUND OF THE INVENTION

This invention relates to an improved fluid T-coupling filter system. A fluid T-coupling typically has first and second fluid flow channels which are generally perpendicular to, and in communication with, one another. The second fluid flow channel opens into a side of the first fluid flow channel so as to form a "T".

One particular use of the T-coupling filter system of this invention is with a PHACO-EMULSIFIER aspirator during eye surgery. The aspirator is used to remove waste and body fluids from a cavity in the eye. Because of the extremely small volume of this cavity and the fragile nature of the eye tissue, it is critical that enough pressure be present within the cavity to keep it inflated so that the opposing surfaces within the cavity do not rub against one another. It is also critical that high levels of pressure be avoided within the cavity as this could cause the cavity to rupture, resulting in severe tissue damage.

The PHACO-EMULSIFIER aspirator is typically utilized in conjunction with a surgical irrigation/aspiration handpiece. The irrigation channel of the irrigation/aspiration handpiece is connected to a pressurized source of irrigation solution by means of disposable surgical tubing. Before the irrigation/aspiration handpiece is connected to pressurized irrigation reservoir, the connecting tubing is threaded through an irrigation valve on the PHACO-EMULSIFIER aspirator. The valve selectively applies or release pressure on the exterior of the surgical tubing in order to control the flow of the irrigation solution from the irrigation reservoir to the irrigation/aspiration handpiece.

The aspiration channel of the irrigation/aspiration handpiece is connected to a drainage reservoir by means of disposable surgical tubing. A vacuum within the aspiration line is created by means of vacuum pump roller assembly. Before the irrigation/aspiration handpiece is connected to the drainage reservoir the connecting surgical tubing is threaded through a vacuum pump roller assembly. The vacuum pump consists of plural radially extending arms with small rollers at their outer edges. As the arms rotate about a central axis, the rollers pinch the surgical tubing against the flat outer wall of the vacuum pump roller assembly in create a suction at the handpiece tip.

If the inlet of the aspiration channel occludes, the vacuum pump roller assembly could theoretically create an unlimited level of vacuum within the tubing. In order to avoid this dangerous situation, a fluid T-coupling is used to connect the surgical tubing connected to the irrigation/aspiration handpiece to the surgical tubing which is threaded through the vacuum pump roller assembly. The first flow channel of the T-coupling is coincident with the aspiration channel and permits body fluids to flow from the surgical site to the drainage reservoir. The second flow channel, commonly called the vacuum vent, is connected to the vacuum vent of the PHACO-EMULSIFIER aspirator which releases the vacuum when predetermined suction or vacuum level is reached.

The irrigation/aspiration handpiece is typically controlled by means of a foot pedal. When the pedal is depressed, the vacuum pump rollers rotate, thereby creating suction at the handpiece tip. When the pedal is released, the rollers stop. However, during the aspiration process, the vacuum created within the surgical tubing connecting the pump and the handpiece causes the tubing to constrict along its entire length. When the rollers stop, the natural tendency of the resilient surgical tubing is to spring back to its original diameter. This creates a momentary residual source of vacuum at the handpiece tip. As it is often critical that the vacuum at the handpiece tip be ceased immediately in order to prevent the delicate eye tissue from being damaged, the foot pedal is connected to a solenoid and a delay timer which open the vacuum vent of the PHACO-EMULSIFIER aspirator for one quarter of a second in order to release this residual vacuum yet prevent the aspirated waste fluids from flowing back through the tubing and contaminating the eye cavity.

It is critical that the aspiration channel of the T-coupling is not blocked by the tissue fragments or coagulating blood, otherwise the resulting improper level of vacuum at the surgical site could cause body tissue damage. It is also necessary that the vent path be kept free of blockage as this could cause the level of vacuum communicated to the surgical site to exceed safe levels. Furthermore, it is critical that the connection of the fluid T-coupling to the vent path is consistently accurate, since any misalignment between the fluid T-coupling in the vent path will result in a change in the vacuum level of the system and therefore create the risk of damaging the eye tissue.

A disposable fluid T-coupling presently being used with such a PHACO-EMULSIFIER aspirator is described in U.S. Pat. No. 4,418,944. This fluid T-coupling has a nozzle shaped body with a protruding tab. One of the connecting tubes fits coaxially over one end of the nozzle body and the other fits coaxially into the other end of the nozzle body. This body is then inserted into a mating receptacle in the PHACO-EMULSIFIER aspirator and is rotated about an axis parallel to the axis of the nozzle body and therefore the connecting tubes. The protruding tab serves to linearly align the fluid T-coupling properly within the receptacle. Cam surfaces on the body of the fluid T-coupling and on the surface of the receptacle cooperate to press the vent opening on the fluid T-coupling against the vent opening in the surface of the receptacle in order to provide a seal.

There are concerns, however, which are not provided for at all by the T-couplings presently available. It is critical that bacteria and minute particles entrained in the air entering through the vent path do not cause the contamination of the transmitted body fluids or the surgical site. Furthermore, if tissue or coagulated blood becomes lodged in the vent path it could cause the body fluids to be aspirated at an improper rate. The presence of tissue or coagulated blood in the vent path could also cause contamination. Such contamination occurs when the trapped material decomposes or breeds harmful organisms which subsequently contaminate the transmitted body fluid or the surgical site.

Although the use of disposable fluid T-couplings helps reduce the likelihood of such contamination, it does not eliminate the threat. The vent path can still be contaminated by coming in contact with a contaminated area of the non-disposable portion of the vent path. Contamination is also possible as a result of contact with the atmosphere through the opening of the disposable portion of the vent path during the replacement of the disposable fluid T-coupling.

In an attempt to prevent contamination from the vented air, filters are often inserted on the vent line and connected to the fluid T-coupling by flexible tubing. The use of these filters, and their corresponding filter lines, often leads to a confusing array of interconnecting tubes which easily become entangled and can be unreasonably difficult to connect. A simple reliable fluid T-coupling which assures its proper alignment and prevents contamination is therefore needed.

SUMMARY OF THE INVENTION

A fluid T-coupling, comprising a through fluid flow path, and an intersecting vent path, wherein the vent path is integrally molded within a filtered bayonet connector to be used with an aspirator, such as a PHACO-EMULSIFIER aspirator, to control the level of vacuum communicated to an irrigation/aspiration handpiece during eye surgery. The bayonet connector consists of a cup and a disc-shaped cap which firmly hold a disposable filter between them. The outer portion of the filter cap comprises an axial cylindrical projection which has a distally-located nipple and is preferably surrounded by a resilient sealing member. The bayonet connector can be inserted into, and sealably connected to a bayonet receptacle in a PHACO-EMULSIFIER aspirator. Tabs on the side of the filter casing cooperate with mating surfaces of the receptacle to lock the molded coupling into place, and create a fluid-tight seal.

A twist locking handle may be molded onto the T-coupling opposite the bayonet connector. This handle allows the operator to twist the locking tabs into place without touching the T portion of the coupling. This minimizes the likelihood that the T-coupling will be damaged or contaminated.

The bayonet connector provides a means for quickly and easily aligning the vent paths by using the paths themselves to aid alignment.

In order to ensure the correct alignment of the molded coupling, the tabs and their corresponding notches in the receptacle for receiving them can be of diverse shape so as to allow insertion of the bayonet connector only if it is correctly oriented.

The combined T-coupling, filtered bayonet connector, and handle provides a lightweight and compact assembly which was heretofore unavailable. This assembly can be integrally molded out of plastic so as to make the cost sufficiently low that the assembly can be disposable. The use of such a disposable assembly minimizes the possibility of contamination inherent in the use of previously available units.

DESCRIPTION OF THE DRAWINGS

These and other features of the invention will now be described with reference to drawings of the preferred embodiment which is intended to illustrate, but not to limit the invention, and in which.

DESCRIPTION OF THE PREFERRED EMBODIMENT

This invention relates to fluid couplings used with an ocular aspiration machine, such as a PHACO-EMULSIFIER aspirator.

Figure 1:
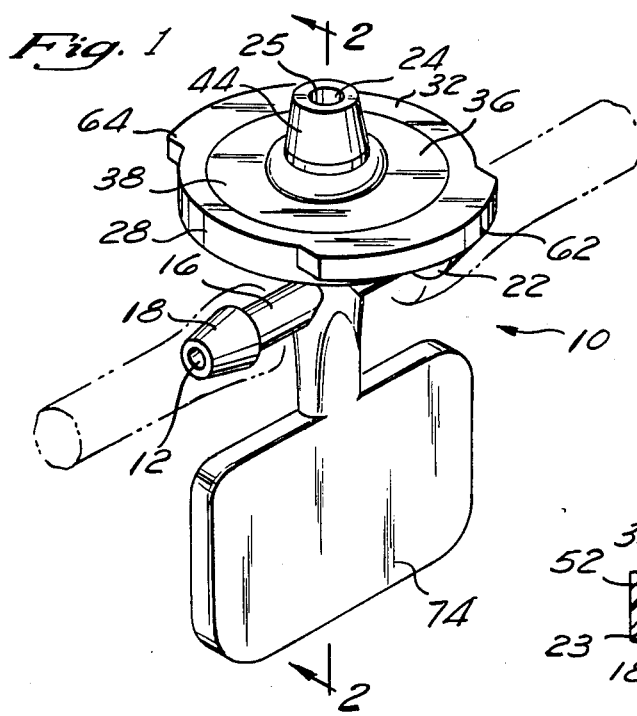
FIG. 1 is a perspective view of the filtered T-coupling of the present invention.
Figure 2:
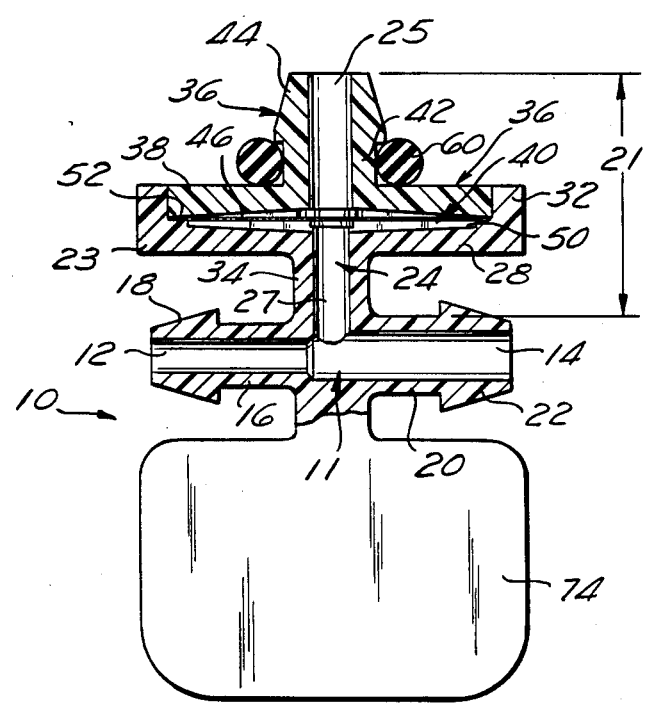
FIG. 2 is a partial sectional view taken along 2—2 of FIG. 1 showing the fluid flow channels.

Referring to FIGS. 1 and 2, there is shown a fluid T-coupling 10 embodying this invention. The fluid T-coupling 10 has a substantially linear through-flow fluid path 11 comprised of an inlet channel 12 and an outlet channel 14 (FIG. 2). Preferably, the inlet channel 12 is of smaller diameter than, but substantially coaxial with, outlet channel 14. The larger diameter of the outlet channel 14 helps ensure that any particles contained in the body fluids drawn through the inlet channel 12 will not become lodged in the fluid T-coupling 10.

The inlet channel 12 forms a central cylindrical bore through a cylindrical inlet 16 and an inlet nipple 18. The inlet nipple 18 has the external appearance of a truncated cone, with the base of the cone being of larger diameter than the cylindrical inlet 16. Thus, a piece of surgical tubing, such as shown in phantom in FIG. 1, can be slideably forced over the inlet nipple 18 to form a fluid tight connection with the inlet nipple 18.

In a similar manner, the outlet channel 14 forms a central cylindrical bore through a cylindrical outlet 20 and an outlet nipple 22. The outlet nipple 22 has the external appearance of a truncated cone, with the base of the cone being of larger diameter than the cylindrical outlet 20. Thus, a piece of surgical tubing, such as shown in phantom in FIG. 1, can be slideably forced over the outlet nipple 22 to form a fluid tight connection with the outlet nipple 22.

In practice, the tubing connected to the inlet nipple 18 is sealably connected to an irrigation/aspiration surgical handpiece, thereby permitting the communication of the inlet channel 12 with the surgical site. The tubing connected to the outlet nipple 22 is sealably connected to a drainage reservoir and vacuum is created within the tubing by means of a vacuum pump roller assembly, thus permitting fluid to be drawn from the surgical site through the connecting tubing, the inlet channel 12, and the outlet channel 14 to the drainage reservoir.

Communicating with the inlet and outlet channels, 12 and 14, is a substantially linear vent path 24, comprised of an inflow channel 25 and an outflow channel 27. The vent path 24 intersects and is generally perpendicular to the through fluid flow path 11 comprised of inlet channel 12 and outlet channel 14.

Preferably, the outflow channel 27 opens into the side of the outlet channel 14, rather than the smaller inlet channel 12, thereby decreasing the likelihood of the intersection between the through flow path 11 and the vent path 24 being obstructed. It is likewise preferable, to prevent turbulence, that the axis of the outlet channel 14 and the axis of the outflow channel 27 essentially intersect.

During surgery, the vent path 24 communicates with the vent path of the PHACO-EMULSIFIER aspirator, the inlet channel 12 communicates with the surgical site, and the outlet channel 14 communicates with a drainage reservoir. By controlling the amount of air introduced through the vent path 24, the resulting suction exerted on the inlet channel 12, and therefore on the surgical site, can be regulated. If the vent path 24 is blocked so that no air is allowed in, then the amount of vacuum at the surgical site will be maximized. Conversely, if the vent path 24 provides substantially less resistance than the inlet channel 12, air will be drawn through the vent path 24 rather than through the inlet channel 12 with the result that there will be a substantial reduction in the level of suction provided to the surgical site.

When the foot pedal control of the PHACO-EMULSIFIER aspirator is released, a solenoid and a delay timer open the vent path of the PHACO-EMULSIFIER aspirator for one quarter of a second in order to prevent the constricted surgical tubing, as it springs back to its normal diameter, from creating unwanted suction at the tip of the irrigation/aspiration handpiece and potentially damaging the delicate eye tissue.

Figure 3:
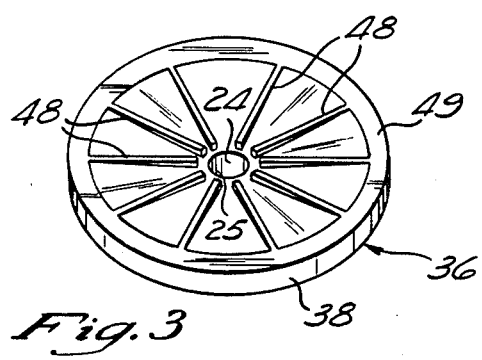
FIG. 3 is a perspective view of the mating portion of the cap.
Figure 4:
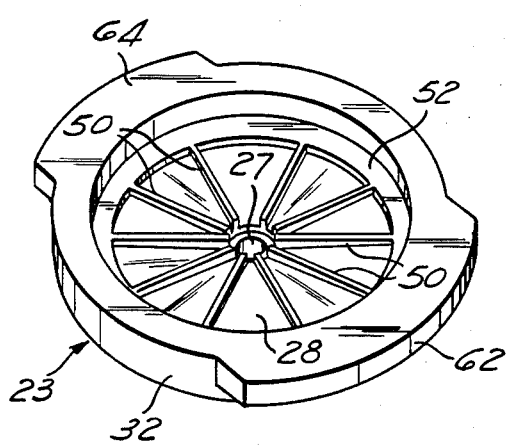
FIG. 4 is a perspective view of the mating portion of the cup.

Referring to FIGS. 2-4, there is shown the vent path 24 integrally molded within a filtered bayonet connector 21. The bayonet connector 21 comprises a retaining cup 23 and a cap 36. The retaining cup 23 is defined by a generally disc-shaped base 28 and a peripheral annular flange 32. The cup 23 is connected to the cylindrical inlet and outlet, 16 and 20, by means of an axial, cylindrical protrusion 34 extending opposite the annular flange 32. The outflow channel 27 forms an axial cylindrical bore through the protrusion 34. Preferably all of the above parts are molded to form a single unit.

One end of the outflow channel 27, and thus the vent path 24, opens into the side of the outlet channel 14. The other end of the outflow channel 27 opens into a generally cylindrical filter cavity 40 whose bottom and sides are defined by the base 28 and the flange 32, respectively.

A cap 36, having a generally disc-shaped foundation 38 and an axial cylindrical projection 42, is positioned so that its foundation 38 fits tightly within the peripheral annular flange 32 of the cup 23 and its projection 42 extends opposite the cavity 40. The cap foundation 38, thus serves to define the roof of the filter cavity 40.

The end of the projection 42 distal the cap's foundation 38 has a nipple 44 which has the external appearance of a truncated cone, with the base of the cone being of larger diameter than the cylindrical projection 42. The inflow channel 25 forms an axial cylindrical bore through the projection 42 and the projection nipple 44. Thus, the inflow channel 25 communicates with the filter cavity 40.

Referring to FIGS. 3 and 4, there is shown the mating portions of the cap 36 and the cup 23, respectively. Referring to FIG. 3, there are plural projections such as ribs 48 extending radially from the mouth of the inflow channel 25. The height of the ribs 48 decreases as the distance from the inflow channel 25 increases. There is a rim 49 at the periphery of the cap foundation 38. The ribs 48 are substantially the same height as the rim 49 at their juncture so that the ribs 48 essentially blend into the rim 49.

Referring to FIG. 4, there are also radially oriented ribs or spokes 50 extending from the mouth of the outflow channel 27 towards the base's peripheral flange 32. There is a peripheral rim 52 located at the intersection of the flange 32 and the base 28. The spokes 50 are of substantially the same height as the rim 52 so that the spokes 50 essentially blend into the rim 52 at their juncture.

The cap foundation 38 and the cup's peripheral flange 32 secure the filter 46 within the cavity 40 and are bonded together by adhesives or ultrasonic bonding. Thus bonded, the cap foundation 38 fits wholly within the peripheral flange 32 of the cup 23, and the cup rim 52 cooperates with the cap rim 49 to ensure that an airtight seal is created at the outer periphery of the filter 46. In essence, the filter 46 acts like a gasket between the cap 36 and the base 28 to aid the rims, 49 and 52, in forming a fluid-tight seal. The ribs 48 and spokes 50, act to space the filter 46 from the mouth of the inflow channel 25 and the mouth of the outflow channel 27, respectively so as to prevent a seal from forming between the filter 46 and edges of the mouth of either channel. The spaces between the ribs 48 near the mouth of the inflow channel 25 and the spokes 40 near the mouth of the outflow channel 27 permit the free flow of air over the entire surface of the filter 46 and ensure that the entire filter surface will be utilized.

It is thus clear that the air drawn into the mouth of the inflow channel 25 adjacent the nipple 44 will pass through the filter 46 before reaching the outflow channel 27. This will prevent any entrained particles or bacteria from entering the outlet channel 14 from the outflow channel 27 and thus will prevent the contamination of both the transmitted body fluids and the surgical site.

The connection of the fluid coupling 10 to an aspirator will be described with reference to FIG. 5. The vent path 24 could be connected to the aspirator via a flexible surgical tubing, but is preferably connected to the aspirator by a more sturdy means such as described hereinafter.

Figure 5:
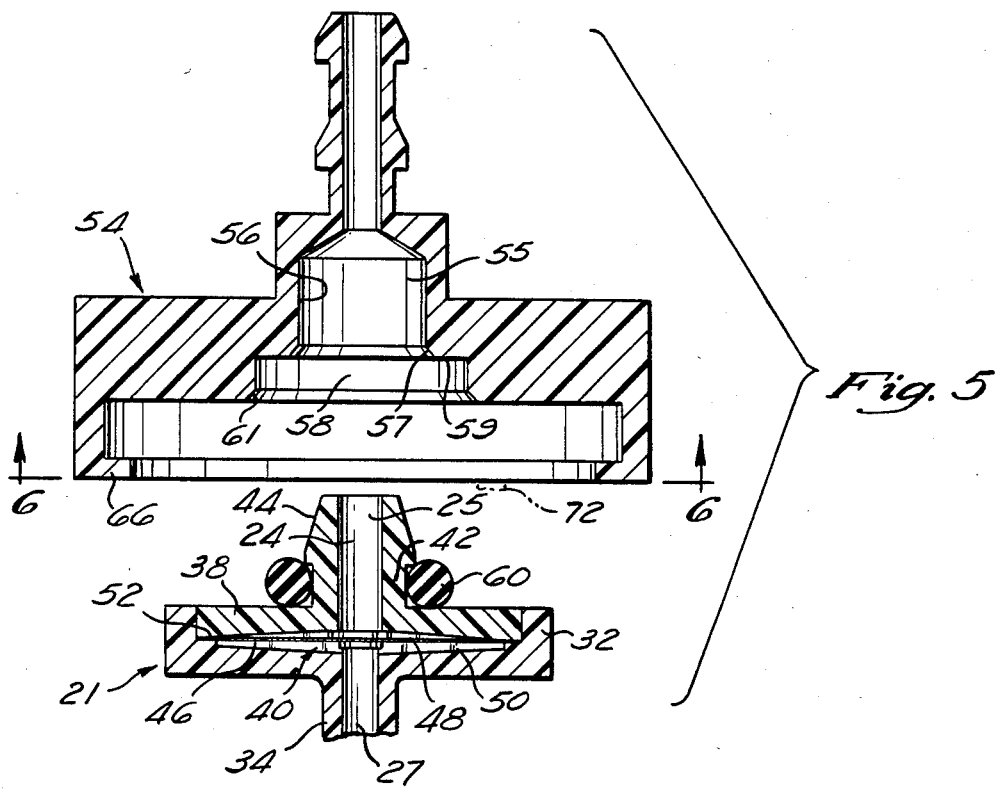
FIG. 5 is a sectional view of the receptacle and the filtered bayonet of the T-coupling.

FIG. 5 is a sectional view illustrating the bayonet connector 21 of the coupling 10 and a bayonet receptacle 54 on the aspirator. The receptacle 54 has an alignment cavity 55, defined by a cylindrical surface 56, shaped to removably receive the nipple 44 which contains the inflow channel 25. Preferably, the cavity 55 will be slightly larger than the nipple 44 so that the cylindrical surface 56 will serve to center and align the fluid coupling 10, but not provide a sealing contact with the fluid coupling 10.

Adjacent the cavity 55 there is preferably an outwardly tapering surface 57 which will further serve to center and align the coupling 10. Adjacent the tapered surface 57 is a sealing cavity 58, which has a greater diameter than the alignment cavity 55 and is partially defined by a donut-shaped sealing surface 59. A second outwardly tapering surface 61 further aids in centering and aligning the bayonet connector 21 within the receptacle 54.

When the bayonet connector 21 is directly connected to the aspirator, an O-ring 60 or other suitable resilient sealing surface is placed over the vent path nipple 44 so that, upon the proper alignment of the coupling 10 within the receptacle 54, the O-ring 60 will engage the receptacle's sealing surface 59 and thereby create an airtight seal.

Referring now to FIG. 1, a large and a small tab, 62 and 64, extending from the peripheral flange 32 essentially comprise segments of an arc, having a thickness less than the height of the peripheral flange 32, and extending substantially radially outward from the axis of the cup base 28.

Referring again to FIGS. 5 and 6, the receptacle 54 has a depending, peripheral overhanging flange 66 of L-shaped cross-section which contains a large notch 68 which corresponds in size and shape to the large tab 62, and a small notch 70, which corresponds in size and shape to the small tab 64. This allows the tabs, 62 and 64, when correctly oriented, to be inserted through their respective notches, 68 and 70, so that the bayonet connector 21 can be rotated about the axis of the vent path 24 to lock the tabs, 62 and 64, beneath the overhanging flange 66.

The use of the two diversely sized and/or shaped tabs, 62 and 64, in combination with their corresponding notches, 68 and 70, ensures that the bayonet connector 21 will be inserted into the receptacle 54 in only one, correct orientation.

Figure 7:
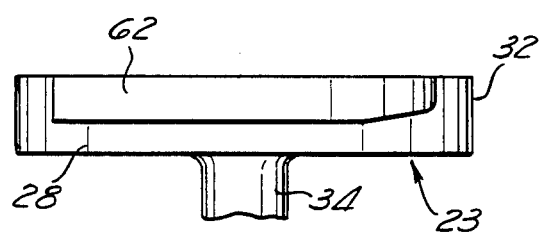
FIG. 7 is a side view of the cap illustrating the tapered edge of a tab.

As shown in FIG. 7, the leading edges of the tabs, 62 and 64, can be tapered to facilitate their insertion beneath the overhanging flange 66.

Figure 6:
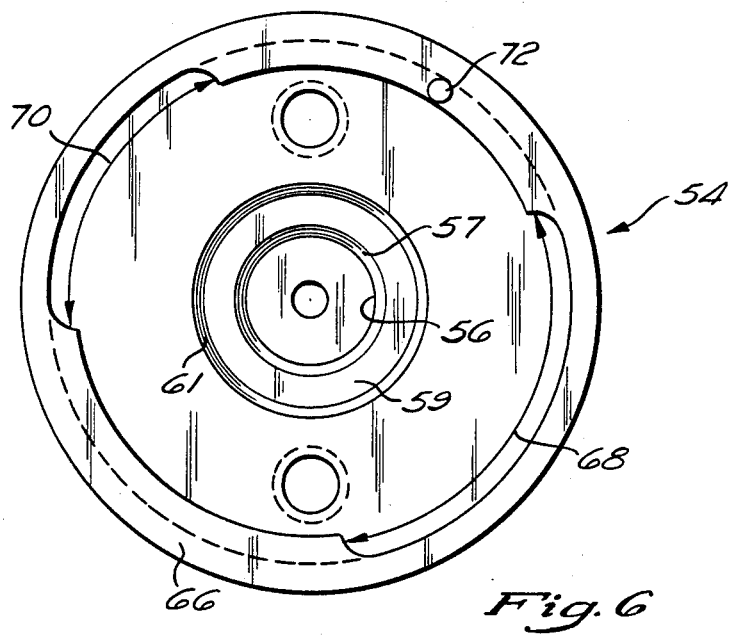
FIG. 6 is a view of the receptacle taken along 6—6 of FIG. 5.

FIG. 6 illustrates the use of a pin 72 secured between the overhanging flange 66 and the body of the receptacle 54. So secured, the pin 72 will contact the leading edge of the small tab 64 to prevent the further rotation of the bayonet connector 21 once it is correctly aligned. The pin 72 will also serve to ensure that the bayonet connector 21 is rotated in the correct direction. If the bayonet connector 21 is rotated in the wrong direction, the pin 72 will contact the edge of the large tab 62 and prevent the further rotation of the fluid coupling 10. The tabs, 62 and 64, are sized and spaced so that the improper alignment of the coupling 10 will be easily visually discernable when the pin 72 is in contact with the large tab 62.

The connection between the tabs, 62 and 64, and the receptacle 54, is sufficiently sturdy so as to provide a solid support for the fluid coupling 10. Thus, the tendency of the rotating arms of some vacuum pump assemblies to draw on the tubing connected to the outlet nipple 22 will not cause the vent path seal to break. Furthermore, a sturdy support for the fluid coupling 10 will tend to decrease the likelihood that the connecting tubing will become detached from the inlet and outlet nipples, 18 and 22.

FIGS. 1 and 2 illustrate the use of a handle 74 connected to the cylindrical inlet and outlet, 16 and 20, and preferably integrally molded with them. In the illustrated embodiment, the handle 74 takes the shape of a thin, rectangular member which is large enough to be easily grasped by a thumb and forefinger.

In practice, it is possible to grasp the cylindrical inlet and outlet 16 and 20, and the corresponding inlet and outlet nipples 18 and 22, in order to rotate the fluid coupling 10 and lock the tabs 62 and 64 of the bayonet connector 21 into the receptacle 54. However, if the connecting tubes are not in place, grasping these components may contaminate the nipples, 18 and 22. If the tubes are already attached to the nipples, 18 and 22, then grasping them may disrupt the fluid tight seal and allow leakage or contamination of the tubing. The handle 74 provides a rigid accessible surface which can be used to insert the bayonet connector 21 into the receptacle 54 without the risk of contamination, or compromising the connection of flexible tubing to the nipples, 18 and 22.

Preferably, the fluid coupling 10 is molded as a two piece unit out of plastic, except for the filter 46 and the O-ring 60. This allows the fluid coupling 10 to be readily molded and manufactured at a cost which allows the entire fluid coupling 10 to be disposable.

Thus, there is advantageously provided an integrally molded unit which provides an easily replaceable T-fluid coupling with an integral filter and an alignment means which assures the correct alignment of the fluid coupling 10 with the receptacle 54 of the aspirator and locks and seals the coupling 10 to the machine. All these features are combined into one integral unit which is disposable so as to minimize the hazard of contamination.

I claim:

1. A fluid T-coupling system, comprising:
   a filtered fluid T-coupling, comprised of;
      a substantially linear through fluid flow path having an outlet channel and an inlet channel,
      a substantially linear vent path having an inflow channel and an outflow channel, said outflow channel intersecting and communicating with said through fluid flow channel,
      a filter, at least a portion of which is sealed within said T-coupling, wherein said portion of said filter sealed within said T-coupling is positioned between said inflow and outflow channels in such a manner that all fluid flowing from said inflow channel to said outflow channel passes through said portion of said filter,
      a sealing surface circumventing said inflow channel, and
      two peripheral tabs connected to said vent path in a plane essentially perpendicular to said inflow channel; and
   a receptacle to which said T-coupling is selectably lockable, comprised of;
      a vent channel having an inlet and an outlet, said inlet communicating with an air supply,
      a sealing surface circumventing said vent channel outlet designed to mate with said sealing surface of said T-coupling, and
      a peripheral overhanging flange of generally L-shaped cross-section connected to said vent channel outlet, the overhanging portion of said flange including notches through which said tabs can be inserted in a direction essentially parallel to said vent path of said T-coupling, said overhanging flange having a height greater than the height of said tabs, thereby permitting said tabs after said insertion to be rotated about the longitudinal axis of said vent path to lock said tabs beneath said overhanging flange and causing said mating sealing surfaces to form an airtight seal between one another while permitting the communication of said receptacle vent outlet with said T-coupling inflow channel.

2. The fluid T-coupling system of claim 1 wherein one of said tabs has a shape which allows it to be inserted through only one of said notches in a direction parallel to said vent path.

3. The fluid T-coupling system of claim 1 further comprising a handle extending opposite said filter from said intersection of said flow path and said vent path to facilitate the rotation of said fluid T-coupling.

4. The fluid T-coupling system of claim 2 further comprising a pin secured between said overhanging flange and said receptacle thereby limiting the range of potential axial rotation of said T-coupling within said receptacle.

5. The fluid T-coupling system of claim 1 wherein said tabs are tapered to facilitate their rotation within said receptacle.

6. A filtered T-coupling selectably lockable with a receptacle, said receptacle forming a fluid flow channel and having a generally L-shaped overhanging flange, the overhanging portion of which has two notches formed therein, comprising:
   a first through fluid flow channel;

a second substantially linear fluid flow channel intersecting said first channel, said second channel intersected by a cavity distal said intersection of said first and second channels;

a filter at least a portion of which is sealed within said T-coupling, wherein said portion of said filter sealed within said T-coupling is positioned within said cavity so as to completely permeably block said second channel; and two tabs extending outward from said second channel in a plane essentially perpendicular to said second channel less than the distance said flange of said receptacle overhangs, so as to be insertable through said notches in a direction essentially parallel to said second channel, said tabs having a thickness which permits said tabs, after said insertion through said notches, to be rotated about the axis of said second channel to lock said tabs beneath said overhanging flange of said receptacle, thereby permitting the communication of fluid between said receptacle fluid flow channel and said second fluid flow channel.

7. The filtered T-coupling of claim 6 further comprising a resilient sealing surface circumventing said second channel designed to form a seal with a mating sealing surface on said receptacle.

8. The filtered T-coupling of claim 6 wherein the two tabs essentially comprise segments of an arc.

9. The filtered T-coupling of claim 6 wherein the larger of said two tabs is not insertable in a direction parallel to said second channel through one of said notches, thus further ensuring the correct orientation of the fluid T-coupling within the receptacle.

10. The filtered T-coupling of claim 6 wherein the tabs are tapered in the direction in which they are properly to be rotated upon insertion.

11. The filtered T-coupling of claim 6 further comprising an essentially planar handle extending opposite said filter from said intersection of said first and second channels, said handle oriented so that the line of the axis of said second channel is contained within the plane of said handle, thereby facilitating the rotation of the T-coupling about the axis of said second channel.

12. The filtered T-coupling of claim 6 wherein said surfaces defining said cavity have ribs to aid in fixedly securing said filter within said cavity.

13. The filtered T-coupling of claim 6, wherein the ends of said first channel have truncated cone-shaped nipples to ensure a fluid-tight seal between a connecting tube and said coupling.

* * * * *